(12) United States Patent
Gerhardt et al.

(10) Patent No.: US 7,311,502 B2
(45) Date of Patent: Dec. 25, 2007

(54) METHOD FOR USING A HYDRAULIC AMPLIFIER PUMP IN ULTRAHIGH PRESSURE LIQUID CHROMATOGRAPHY

(75) Inventors: Geoff C. Gerhardt, Milbury, MA (US); Bruce J. Compton, Lexington, MA (US)

(73) Assignee: Waters Investments Limited, New Castle, DE (US)

( * ) Notice: Subject to any disclaimer, the term of this patent is extended or adjusted under 35 U.S.C. 154(b) by 751 days.

(21) Appl. No.: 10/791,080

(22) Filed: Mar. 1, 2004

(65) Prior Publication Data

US 2004/0170510 A1    Sep. 2, 2004

Related U.S. Application Data

(63) Continuation of application No. 10/026,089, filed on Dec. 21, 2001, now Pat. No. 6,712,587.

(51) Int. Cl.
*F04B 17/00*    (2006.01)

(52) U.S. Cl. .................. 417/390; 91/321; 417/388

(58) Field of Classification Search ............... 417/390, 417/387, 388, 401, 403; 91/321, 275, 415
See application file for complete search history.

(56) References Cited

U.S. PATENT DOCUMENTS

| | | | | | |
|---|---|---|---|---|---|
| 4,003,679 | A | * | 1/1977 | McManigill | 417/246 |
| 4,684,465 | A | * | 8/1987 | Leaseburge et al. | 210/198.2 |
| 5,092,745 | A | * | 3/1992 | Graham | 417/401 |
| 6,017,200 | A | * | 1/2000 | Childs et al. | 417/404 |
| 6,712,587 | B2 | * | 3/2004 | Gerhardt et al. | 417/390 |
| 6,929,454 | B2 | * | 8/2005 | Munzenmaier et al. | 417/403 |
| 7,163,359 | B2 | * | 1/2007 | Moser | 406/74 |
| 2003/0133810 | A1 | * | 7/2003 | Leppin et al. | 417/254 |

* cited by examiner

*Primary Examiner*—William H. Rodriguez
(74) *Attorney, Agent, or Firm*—Anthony J. Janiuk

(57) ABSTRACT

A method for supplying solvent to an ultra-high pressure liquid chromatography system using a hydraulic amplifier. The hydraulic amplifier system includes a hydraulic cylinder comprising a primary piston chamber in which a primary piston is disposed and a secondary piston chamber in which a secondary piston is disposed. The cross-sectional area of the primary piston is larger than the cross-sectional area of the secondary piston. The difference in the cross-sectional areas of the pistons creates an amplification of the pressure in the primary piston chamber and a reduction in flow rate.

23 Claims, 3 Drawing Sheets

METHOD FOR USING A HYDRAULIC AMPLIFIER PUMP IN ULTRAHIGH PRESSURE LIQUID CHROMATOGRAPHY

CROSS REFERENCE TO RELATED APPLICATIONS

This application is a continuation of application Ser. No. 10/026,089 filed Dec. 21, 2001, now U.S. Pat. No. 6,712,587. The contents of the aforementioned application are hereby expressly incorporated herein by reference in its entirety.

FIELD OF THE INVENTION

The present invention relates to a pump for ultra-high pressure liquid chromatography, and more particularly to a pump to generate the high pressure and low flow rates required for ultra-high pressure liquid chromatography.

BACKGROUND OF THE INVENTION

Pumps used in typical high pressure liquid chromatography (HPLC) generate approximately 5000 psi. These pumps, which typically use mechanical mechanisms to actuate flow-generating pistons, cannot create the pressures required for ultra-high pressure liquid chromatography (UHPLC), which operates at pressures in excess of 25,000 psi. Pneumatic amplifiers have been used to generate high pressures for UHPLC systems. For example, in the paper entitled "Ultra-high-Pressure Reversed-Phase Liquid Chromatography in Packed Capillary Columns," Analytical Chemistry, 1997,69 (6), 983-989, two Haskel pneumatic amplifier pumps are used to perform isocratic LC separations at pressures of 60,000 psi. FIG. 1 shows such a configuration. However, since the gas in pneumatic amplifiers is compressible, pneumatic amplifiers can deliver only constant pressure flow, which precludes high pressure gradient mixing necessary to perform gradient chromatography. That is, in gradient chromatography, two solvents are mixed in varying ratios, thereby requiring constant volume flow of the respective solvents, which cannot be done with pneumatic amplifier pumps. Alternatively, gradient chromatography can be performed by feeding the gradient mixture into a single pump. However, this is difficult to implement at the low flow rates used in UHPLC.

The paper entitled "Ultrahigh-Pressure Reversed-Phase Capillary Liquid Chromatography: Isocratic and Gradient Elution Using Columns Packed with 1.0-m Particles," Analytical Chemistry, 1999,71(3), 700-708, describes a UHPLC system that uses a mechanical actuator rather than a pneumatic actuator. The mechanical actuator comprises an ultra-high-pressure constant-flow syringe pump including an electric motor connected to a gear reduction system and linear actuator that moves a piston. Although the syringe pump can generate operating pressures in excess of 130,000 psi, the mechanical actuator is too large to commercialize effectively.

SUMMARY OF THE INVENTION

The present invention provides a pump that can generate sufficient pressure and that creates substantially constant flow rate in a range sufficient for ultra-high pressure liquid chromatography.

The pump according to the invention comprises a hydraulic amplifier system using hydraulic force to generate high pressures in excess of approximately 30,000 psi and low flow rates of approximately 1 μL/min or less. An HPLC pump is used to pump hydraulic fluid into a primary cylinder of the hydraulic amplifier. The primary cylinder contains a large-diameter piston, which actuates a small-diameter piston contained in a secondary cylinder. Due to the reduction in cross-sectional area of the pistons, the pressure in the primary cylinder is amplified. The amount of pressure amplification is determined by a ratio of the surface areas of the pistons. The reduction in cross-sectional area of the hydraulic amplifier also creates a reduction in flow rate, thereby achieving the desired low flow rate.

Features and advantages of the invention include provision of a pump configuration capable of generating a pressure in excess of approximately 30,000 psi and a flow rate of approximately 1 μL/min or less. The pump configuration according to the present invention is suitable for use in an ultra-high pressure liquid chromatography system and is reliable and easy to manufacture. Standard off-the shelf HPLC pumping technology can be used to control the flow of the primary pumping fluid.

The configuration according to the invention may be implemented to avoid a pressure transducer in a secondary piston. Dead volumes may be advantageously minimized.

The present invention also can be used to perform a gradient separation at constant pressure, for example, when a solvent's compressibility makes accurate flow control difficult.

BRIEF DESCRIPTION OF THE DRAWINGS

The foregoing and other features and advantages of the present invention will be more fully understood from the following detailed description of illustrative embodiments, taken in conjunction with the accompanying drawing in which.

DETAILED DESCRIPTION

Figure 1:
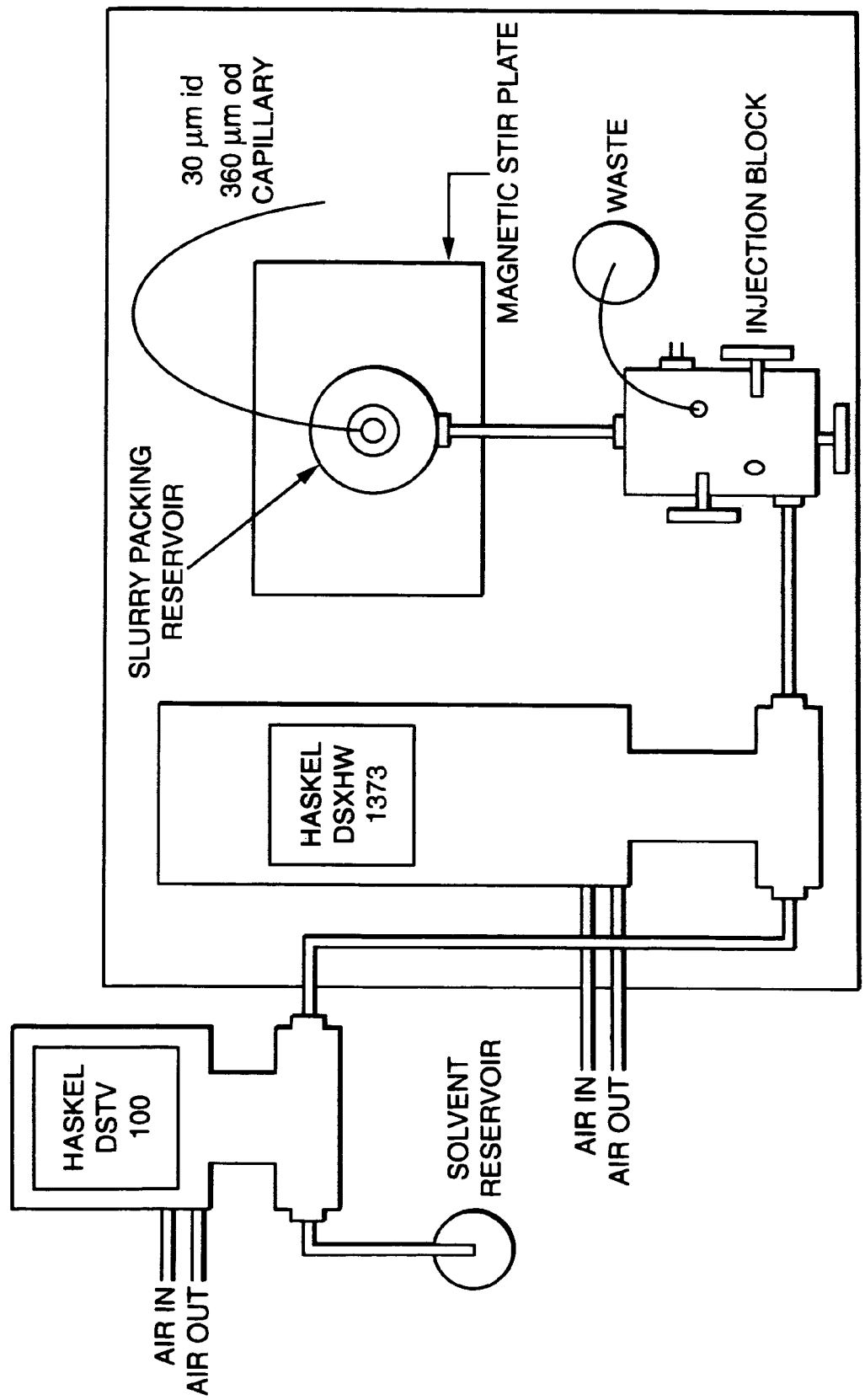
FIG. 1 illustrates an LC system including a pneumatic amplifier pump.
Figure 2:
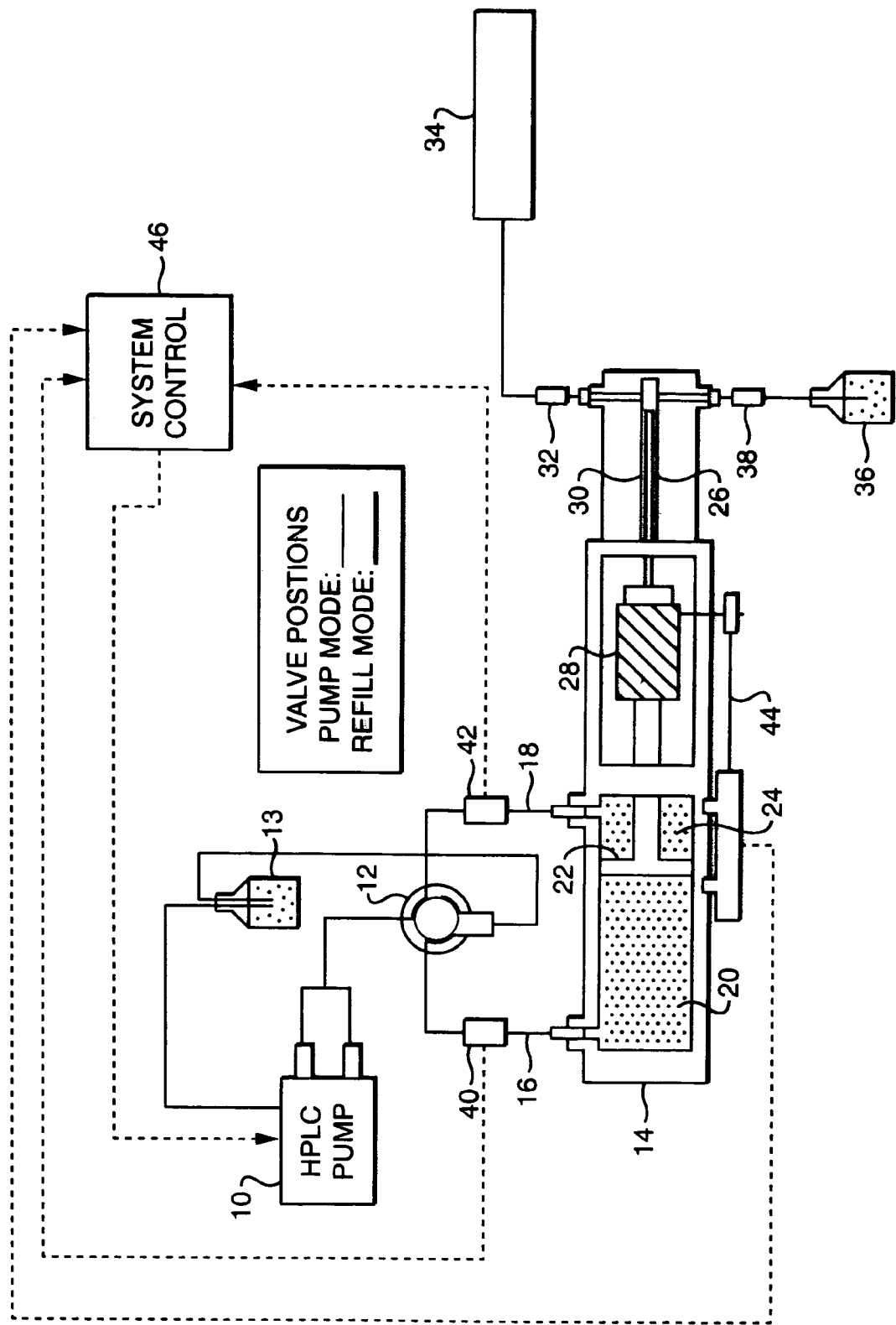
FIG. 2 illustrates a single hydraulic amplifier system.

FIG. 2 shows a schematic of a single hydraulic amplifier system according to the invention. The system comprises HPLC pump 10 which pumps hydraulic fluid through a multi-port HPLC rotary valve 12 into a hydraulic cylinder 14 at a constant flow rate. Excess hydraulic fluid is stored in a hydraulic fluid reservoir 13. The position of the multi-port valve 12 determines whether the hydraulic fluid flows through an inlet valve 16 or outlet valve 18 so as to control whether the HPLC pump operates in "Pump Mode" or "Refill Mode." In the "Pump Mode," hydraulic fluid from the HPLC pump 10 is directed into an inlet chamber 20 of the hydraulic cylinder 14, which displaces a primary piston 22 in a first direction (which in FIG. 2 is to the right). In the "Refill Mode," the hydraulic fluid is directed into an outlet chamber 24, thereby displacing the primary piston 22 in a second direction (which in FIG. 2 is to the left). The primary piston 22 is coupled to a secondary piston 26 through a piston coupler 28.

The primary piston 22 actuates the secondary piston 26 via the piston coupler 28. When the secondary piston 26 is actuated, LC solvent stored in the secondary piston chamber 30 is displaced through a secondary outlet check valve 32 to a chromatography system 34. Excess LC solvent is supplied from a LC solvent reservoir 36 to the secondary piston chamber 30 through a secondary inlet check valve 38.

As shown in FIG. 2, the diameter of the primary piston 22 is larger than the diameter of the secondary piston 26. The differential area provided by the differences in diameter creates a pressure amplification that is proportional to the ratio of the areas. Specifically, if the radius of the primary piston is R1 and the radius of the secondary piston is R2, then the pressure amplification can be calculated as follows:

$$P_2 = (A_1/A_2) * P_1$$

or $$P_2 = (((D_1/2)^2)/((D_2/2)^2)) * P_1$$

Where:
 $P_1$ is the pressure acting on the primary piston,
 $P_2$ is the pressure acting on the secondary piston,
 $A_1$ is the area of the primary piston,
 $A_2$ is the area of the secondary piston,
 $D_1$ is the diameter of the primary piston, and
 $D_2$ is the diameter of the secondary piston.

As an example, if the diameter of the primary piston 22 is 3 cm, and the diameter of the secondary piston 26 is 0.5 cm, then the pressure will be amplified 36 times. That is, if the HPLC pump 10 delivers hydraulic fluid at a pressure of 1389 psi, the pressure in the secondary chamber will be 50,000 psi.

The difference in pressure across the primary piston 22 can be used to determine the pressure delivered by the secondary piston 26 to the chromatography system 34. This is preferable to having a pressure transducer located in the secondary piston chamber 30 because pressure transducers capable of measuring high pressures are difficult to manufacture, add dead volume to the secondary side, and usually require additional fittings to plumb fluidic lines in and out of the transducer. Minimizing dead volume in the secondary side advantageously reduces the time required to pressurize the system. Since the pressure exerted by the secondary piston 26 equals the pressure difference across the primary piston 22 multiplied by the ratio of piston areas, as described above, it is critical that the pressure difference across the primary piston be measured accurately since any errors will by multiplied by this ratio.

The difference in pressure across the primary piston 22 is computed by subtracting the pressure in the outlet chamber 24 of the hydraulic cylinder 14 from the pressure in the inlet chamber 20 of the hydraulic cylinder 14. As shown in FIG. 2, the pressure in the inlet chamber 20 of the hydraulic cylinder 14 is measured by an inlet pressure transducer 40 located at the inlet of the hydraulic cylinder 14 and the pressure in the outlet chamber 24 of the hydraulic cylinder 14 is measured by an outlet pressure transducer 42 located at the outlet of the hydraulic cylinder 14. Positioning the pressure transducers in these positions minimizes the effect of the fluid resistance in the tubing and valves connecting the HPLC pump 10 to the hydraulic cylinder 14 and those connecting the hydraulic cylinder back to the hydraulic fluid reservoir. The pressure transducers 40, 42 alternatively can be disposed in the inlet chamber and the outlet chamber 24, respectively.

In addition to the pressure amplification, the hydraulic amplifier also creates a flow reduction. In the illustrative embodiment, the secondary and primary pistons have substantially identical linear velocities. However, the difference in cross-sectional areas results in a reduction in flow rate.

The reduction in flow rate is computed as follows:

$$F_2 = (A_2/A_1) * F_1$$

or $$F_2 = (((D_2/2)^2)/((D_1/2)^2)) * F_1$$

Where:
 $F_1$ is the primary flow rate,
 $F_2$ is the secondary flow rate,
 $A_1$ is the area of the primary piston,
 $A_2$ is the area of the secondary piston,
 $D_1$ is the diameter of the primary piston, and
 $D_2$ is the diameter of the secondary piston.

As an example, if the diameter of the primary piston is 3 cm, and the diameter of the secondary piston is 0.5 cm, then the flow rate will be reduced 36 times. That is, if the primary flow rate is 0.1 mL/min, the secondary flow rate will be 2.78 uL/min. This reduction in flow rate makes it possible to deliver LC solvent to a chromatography system at a significantly lower flow rate.

Accordingly, by appropriately choosing the piston areas of the primary and secondary piston, a typical HPLC pump can be used to perform capillary UHPLC at the appropriate pressure and flow rate. Also, the back pressure created by the chromatography system for a given flow rate should be determined in order to determine the proper operating pressure for the hydraulic amplifier before delivering metered flow. The back pressure created by the chromatography system can be calculated based upon the size of the particles used in the column, column inner diameter, and solvent viscosity. It is helpful to perform this calculation as a guide, but an experiment is usually done prior to analytical operation of the system to determine the actual operating pressure by allowing the chromatographic system to equilibrate to a stable pressure at the desired flow rate.

A linear position transducer 44 measures the position of the primary and secondary pistons. This information is used by a system controller 46 for various purposes, such as to stop the fluid flow into the hydraulic cylinder 14, switch the rotary valve 12 when the primary piston 22 reaches an end point, calculate the volume of LC solvent dispensed by the secondary piston 26, or calculate the flow rate delivered by the secondary piston 26. A difference between the actual flow rate and an expected value indicates a leakage in the primary system. If this occurs, a feedback system can be used to adjust the primary flow in order to maintain a defined secondary flow.

An automated computer, such as a microcontroller (i.e., embedded system) in communication with a host PC, is used as the system controller 46. The automated computer can be used to control the HPLC pump 10 and the feedback data from the pressure transducers 40, 42 and linear position transducer 44, automatically calculate and display the secondary pressure and piston position, and automatically control the initial pressurization of the system and subsequent metered flow.

Due to the high pressures at which UHPLC is performed and due to the compressibility of the solvent, a significant portion of the piston stroke is used for compressing the solvent. Due to the low flow rates used in UHPLC, it may take some time to compress the LC solvent to the working pressure, and, initially, flow delivery into the chromatographic system will not be proportional to the displacement of the piston. Due to these factors, it is advantageous to run the HPLC pump 10 at a high flow rate until the desired secondary operating pressure has been achieved.

Operation of the hydraulic amplifier 14 can be described as follows. In a refill mode, the hydraulic cylinder 14 is refilled by directing hydraulic fluid from the HPLC pump 10 to the outlet chamber 24 of the hydraulic cylinder 14 in order to drive the primary piston 22 back to a fully retracted position. The retraction of the primary piston 22 draws LC solvent into the secondary chamber 30 through an inlet check valve 38. The HPLC pump 10 is then run in a pump mode at maximum flow until the pressure of the inlet chamber 20 of the hydraulic cylinder 14 reaches the desired operating pressure. Next, the flow of the HPLC pump 10 is changed in order to deliver the desired flow to the chromatographic system 34 through the hydraulic cylinder 14. The position of the primary piston is continuously monitored, so that the HPLC pump can be stopped when the primary piston 22 has reached the end of its stroke.

Figure 3:
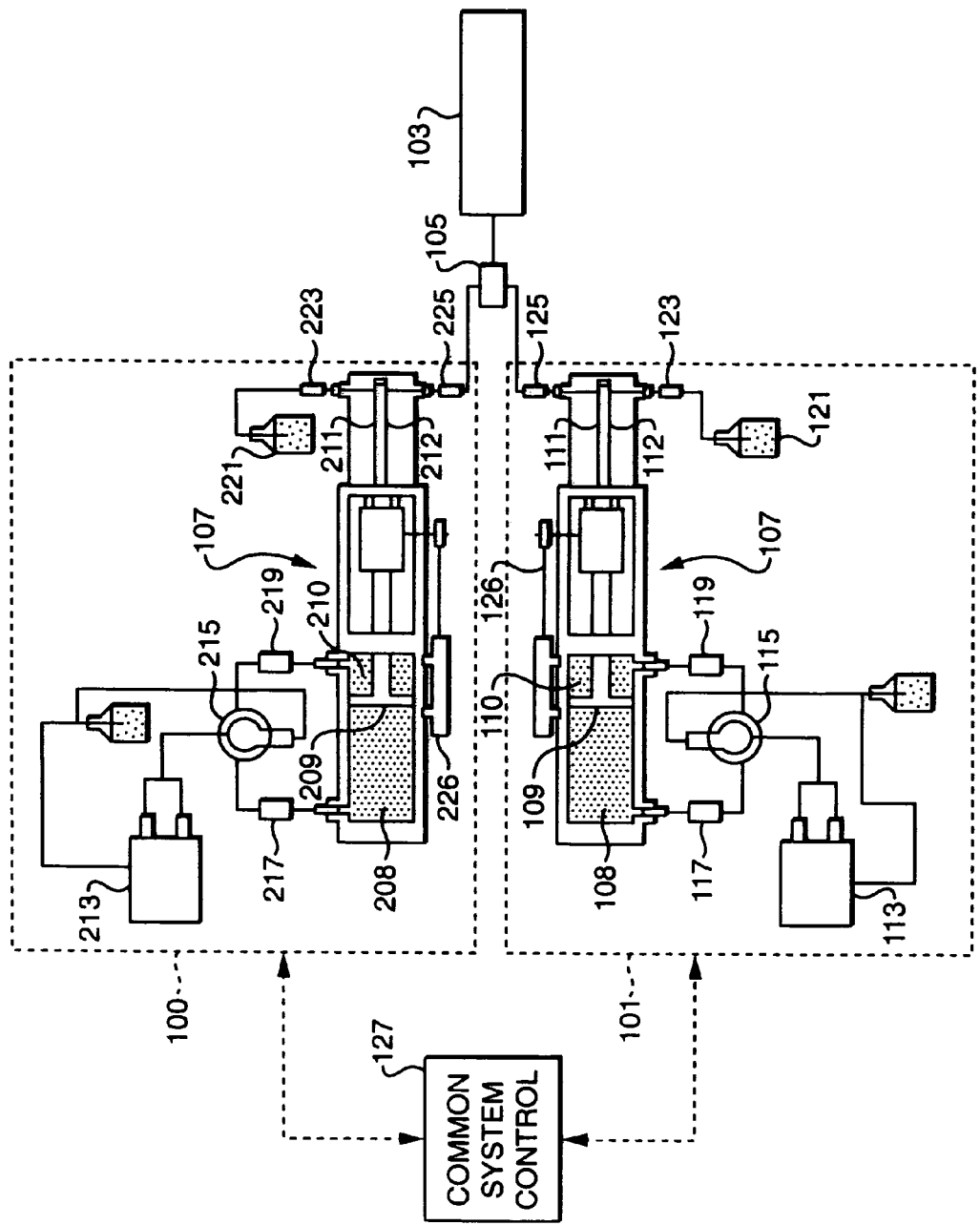
FIG. 3 illustrates a gradient hydraulic amplifier system.

FIG. 3 shows a gradient hydraulic amplifier system that includes two separate hydraulic amplifiers 100, 101 which pump different solvents into the liquid chromatographic system 103 through a mixing chamber 105. In constant flow mode, flow rates of the solvents can be varied such that the solvent composition is varied in a controlled fashion over the course of the chromatographic separation. Each of the hydraulic amplifiers includes a hydraulic cylinder 107 that is substantially similar to the hydraulic cylinder 14 in FIG. 2. For example, each hydraulic cylinder 107 includes an inlet chamber 108/208, primary piston 109/209, outlet chamber 110/210, secondary piston 111/211, secondary piston chamber 112/212, hydraulic pump 113/213, multi-point valve 115/215, primary inlet pressure transducer 117/217, primary outlet pressure transducer 119/219, solvent reservoir 121/221, secondary inlet check valve 123/223, secondary outlet check valve 125/225, and linear position transducer 126/226. A common system controller 127 is used to control and synchronize the operation of the hydraulic amplifiers. The flow rate into the liquid chromatographic system 103 is maintained substantially constant, while the relative flow rates of the different solvents are varied during the chromatographic run in order to deliver a continuously changing solvent gradient to the chromatographic system 103. Although FIG. 3 includes 2 hydraulic amplifiers, additional hydraulic amplifiers can be used for more complex systems.

While the system controller is described herein as a microcontroller (i.e., embedded system) in communication with a host PC, it should be appreciated that only an embedded system, or only a host PC, or the like, could be used.

Although piston position is shown as measured by a single linear position transducer, it should be appreciated that more than one transducer could be used, and/or alternative position sensors implemented, such as a variable resistance element, linear voltage differential transformer (LVDT), optical encoder, or the like. Although the linear position transducer is shown in the drawings as being linked to the interface between the primary and secondary pistons, it may be placed on any part of the primary and secondary pistons, or shafts joining the two.

The present invention also can be used to perform a gradient separation at constant pressure, for example, when a solvent's compressibility makes accurate flow control difficult. In constant pressure mode, the total flow rate delivered by the two hydraulic amplifiers (i.e., in a binary gradient composition) would be varied to maintain a pressure set point. The percentage of this total flow delivered by the hydraulic amplifiers (i.e., the gradient composition) could be changed over the course of a run in order to deliver a gradient.

Although the invention has been shown and described with respect to exemplary embodiments thereof, various other changes, omissions and additions in the form and detail thereof may be made therein without departing from the spirit and scope of the invention.

What is claimed is:

1. A method of supplying solvent to a chromatographic system comprising:
   providing a hydraulic cylinder comprising:
      an inlet chamber;
      an outlet chamber;
      a primary piston disposed between said inlet chamber and said outlet chamber,;
      a secondary piston chamber; and
      a secondary piston disposed in said secondary piston chamber, wherein a cross-sectional area of said primary piston is larger than a cross-sectional area of said secondary piston, such that pressure in said secondary piston chamber is greater than a pressure in said inlet chamber, and a flow rate through said secondary piston chamber is less than a flow rate through said outlet chamber;
   providing a pump, said pump supplying pressurized hydraulic fluid;
   driving said primary piston with said pressurized hydraulic fluid;
   activating said secondary piston by said primary piston;
   moving and pressurizing said solvent; and
   supplying said pressurized solvent to said chromatographic system from said hydraulic cylinder.

2. The method of claim 1 further comprising supplying solvent to said chromatographic system from said hydraulic cylinder at a substantially constant flow rate.

3. The method of claim 1, wherein a ratio of said cross-sectional area of said primary piston to said cross-sectional area of said secondary piston is at least 4:1.

4. The method of claim 1, further comprising measuring the position of said primary piston and said secondary piston with a linear position transducer.

5. The method of claim 1, further comprising regulating hydraulic fluid flow to either said inlet chamber or said outlet chamber with a multiple port valve, thereby controlling said primary piston to operate in one of a pump mode and a refill mode.

6. The method of claim 1, further comprising:
   measuring a pressure in said inlet chamber of said hydraulic cylinder with a first pressure transducer;
   measuring a pressure in said outlet chamber of said hydraulic cylinder with a second pressure transducer; and
   computing a pressure difference across said primary piston and said pressure in said secondary piston chamber using the measurements of said first pressure transducer and said second pressure transducer.

7. The method of claim 6, further comprising said pump supplying said pressurized hydraulic fluid at a high flow rate while said pressure difference is below a threshold and supplying said pressurized hydraulic fluid at a lower flow rate while said pressure difference is at and above said threshold.

8. The method of claim 1, further comprising controlling said hydraulic amplifier system with a system controller.

9. The method of claim 1, further comprising regulating the supply of solvent to said chromatographic system with an outlet check valve.

10. The method of claim 1, further comprising supplying solvent to said secondary piston chamber with an inlet check valve.

11. A method for supplying solvent to a chromatographic system comprising:
- supplying a first pressurized solvent to said chromatographic system with a first hydraulic cylinder;
- supplying pressurized hydraulic fluid at a substantially constant rate from a first pump to actuate a primary piston of said first hydraulic cylinder;
- supplying a second pressurized solvent to said chromatographic system with a second hydraulic cylinder; and
- supplying pressurized hydraulic fluid at a substantially constant rate from a second pump to actuate a primary piston of said second hydraulic cylinder, wherein said first and second hydraulic cylinders comprise:
- an inlet chamber;
- an outlet chamber;
- a primary piston disposed between said inlet chamber and said outlet chamber, said primary piston being driven by said pressurized hydraulic fluid;
- a secondary piston chamber; and
- a secondary piston disposed in said secondary piston chamber, said secondary piston being activated by said primary piston for moving and pressurizing said pressurized solvent;

wherein a cross-sectional area of said primary piston is larger than a cross-sectional area of said secondary piston, such that a pressure in said secondary piston chamber is greater than a pressure in said inlet chamber, and a flow rate through said secondary piston chamber is less than a flow rate through said outlet chamber.

12. The method of claim 11, further comprising said first hydraulic cylinder supplying said first solvent to said chromatographic system at a first constant flow rate and said second hydraulic cylinder supplying said second solvent to said chromatographic system at a second constant flow rate.

13. The method as claimed in claim 11, wherein a ratio of said cross-sectional area of said primary piston to said cross-sectional area of said secondary piston is at least 4:1.

14. The method as claimed in claim 11, further comprising:
- measuring the position of said primary piston and said secondary piston of said first hydraulic cylinder with a first linear position transducer; and
- measuring the position of said primary piston and said secondary piston of said secondary hydraulic cylinder with a second linear position transducer.

15. The method as claimed in claim 11, further comprising:
- regulating hydraulic fluid flow to either said inlet chamber or said outlet chamber of said first hydraulic cylinder with a first multiple port valve, thereby controlling said primary piston of said first hydraulic cylinder to operate in one of a pump mode and a refill mode; and
- regulating hydraulic fluid flow to either said inlet chamber or said outlet chamber of said second hydraulic cylinder with a second multiple port valve, thereby controlling said primary piston of said second hydraulic cylinder to operate in one of a pump mode and a refill mode.

16. The method as claimed in claim 11, further comprising:
- measuring a pressure in said inlet chamber of said first hydraulic cylinder with a first pressure transducer;
- measuring a pressure in said outlet chamber of said first hydraulic cylinder with a second pressure transducer;
- computing a pressure difference across said primary piston of said first hydraulic cylinder using the measurements of said first pressure transducer and said second pressure transducer;
- measuring a pressure in said inlet chamber of said second hydraulic cylinder with a third pressure transducer;
- measuring a pressure in said outlet chamber of said second hydraulic cylinder with a fourth pressure transducer; and
- computing a pressure difference across said primary piston of said second hydraulic cylinder using the measurements of said third pressure transducer and said fourth pressure transducer.

17. The method of claim 16 further comprising:
- said first pump supplying said pressurized hydraulic fluid at a first high flow rate while said pressure difference across said primary piston of said first hydraulic cylinder is below a first threshold;
- said first pump supplying said pressurized hydraulic fluid at a first lower flow rate while said pressure difference across said primary piston of said first hydraulic cylinder is at and above said first threshold;
- said second pump supplying said pressurized hydraulic fluid at a second high flow rate while said pressure difference across said primary piston of said second hydraulic cylinder is below a second threshold; and
- said second pump supplying said pressurized hydraulic fluid at a second lower flow rate while said pressure difference across said primary piston of said second hydraulic cylinder is at and above said second threshold.

18. The method as claimed in claim 11, further comprising controlling said hydraulic amplifier system with a system controller.

19. The method as claimed in claim 11, further comprising:
- regulating the supply of said first solvent to said chromatographic system with a first outlet check valve attached to said first hydraulic cylinder; and
- regulating the supply of said second solvent to said chromatographic system with a second outlet check valve attached to said second hydraulic cylinder.

20. The method of claim 11, further comprising:
- supplying said first solvent to said secondary piston chamber of said first hydraulic cylinder with a first inlet check valve attached to said first hydraulic cylinder; and
- supplying said second solvent to said secondary piston chamber of said second hydraulic cylinder with a second inlet check valve attached to said second hydraulic cylinder.

21. The method of claim 11 further comprising receiving and mixing said first pressurized solvent and said second pressurized solvent in a mixing chamber before supplying said mixed solvents to said chromatographic system.

22. The method of claim 21 further comprising:
- supplying said first solvent to said mixing chamber from said first hydraulic cylinder at a first varying flow rate;
- supplying said second solvent to said mixing chamber from said second hydraulic cylinder at a second varying flow rate; and
- supplying said mixed solvent from said mixing chamber to said chromatographic system at a constant flow rate.

23. The method of claim 11 further comprising:
supplying a third pressurized solvent from a third hydraulic cylinder to said chromatographic system; and
supplying pressurized hydraulic fluid from a third pump at a substantially constant rate to actuate said third hydraulic cylinder, wherein said third hydraulic cylinder has the composition of said first and second hydraulic cylinders.

* * * * *